United States Patent [19]

Dobler et al.

[11] Patent Number: 5,202,445

[45] Date of Patent: Apr. 13, 1993

[54] PREPARATION OF POTASSIUM MAGNESIUM L-ASCORBATE 2-PHOSPHATE

[75] Inventors: Walter Dobler, Heidelberg; Hartwig Voss, Frankenthal; Friedhelm Balkenhohl, Limburgerhof; Joachim Paust, Neuhofen, all of Fed. Rep. of Germany

[73] Assignee: BASF Aktiengesellschaft, Ludwigshafen, Fed. Rep. of Germany

[21] Appl. No.: 747,573

[22] Filed: Aug. 20, 1991

[30] Foreign Application Priority Data

Aug. 24, 1990 [DE] Fed. Rep. of Germany ....... 4026787

[51] Int. Cl.⁵ .......................................... C07D 307/62
[52] U.S. Cl. .................................... 549/315; 549/222
[58] Field of Search ............................. 549/315, 222

[56] References Cited

U.S. PATENT DOCUMENTS

| | | | |
|---|---|---|---|
| 4,179,445 | 12/1979 | Sieb et al. | 549/222 |
| 4,767,870 | 8/1988 | Fujiwara et al. | 549/315 |
| 4,880,786 | 11/1989 | Sasakawa et al. | 514/53 |
| 4,919,921 | 4/1990 | Hatae | 424/62 |
| 4,999,437 | 3/1991 | Dobler et al. | 549/222 |

FOREIGN PATENT DOCUMENTS 0275198  7/1988  European Pat. Off. .
0308918  3/1989  European Pat. Off. .
0388869  3/1990  European Pat. Off. .
77 890/88  5/1990  Japan .

OTHER PUBLICATIONS

Trennung Von Molekularen Mischungen Mit Hilfe Synthetischer Membranen Strathmann, Steinkopff Verlag Darmstadt 1979, pp. 76–86.
Ion Exchange Membranes, D. S. Flett, Ellis Horwood, Chichester, 1983, pp. 179–191.
Chemical Abstracts, vol. 98, No. 9, entry 72675 (1983).
Chemical Abstracts, vol. 110, No. 18, entry 160221 (1989).
Chemical Abstracts, vol. 113, No. 17, entry 152976 (1990).

Primary Examiner—C. Warren Ivy
Assistant Examiner—Raymond Covington
Attorney, Agent, or Firm—Herbert B. Keil

[57] ABSTRACT

Potassium magnesium L-ascorbate 2-phosphate is prepared from an aqueous solution of potassium L-ascorbate 2-phosphate which is highly contaminated with KCl, as is produced in the phosphorylation of 5,6-isopropylidene-L-ascorbic acid, by adding to the solution about 1 equivalent of magnesium ions per equivalent of L-ascorbate 2-phosphate, and subsequently removing the KCl by electrodialysis. The product of this process is a novel salt of L-ascorbic acid 2-phosphate and has very advantageous handling properties.

10 Claims, No Drawings

PREPARATION OF POTASSIUM MAGNESIUM L-ASCORBATE 2-PHOSPHATE

The present invention relates to a process for preparing potassium magnesium L-ascorbate 2-phosphate which is a novel salt of L-ascorbic acid 2-phosphate with properties of great industrial use.

L-ascorbic acid (vitamin C) is a vital part of a balanced human diet and it is standard practice to recommend intake of this vitamin with the diet. However, vitamin C is the least stable vitamin in foodstuffs because it is extremely reactive towards atmospheric oxygen. It is known that ascorbic acid can be made more stable to oxygen and heat by converting it into suitable derivatives. This is particularly important for the recently developed large-scale use of vitamin C in fish farming.

Ascorbic acid monophosphate (AAMP) has the following substantial advantages compared with free ascorbic acid:

1) relatively stable to oxidation,
2) general bioavailability because it is cleaved by phosphatases in vivo and in vitro to ascorbic acid (this has been demonstrated, for example, in guinea pigs, broilers, piglets, Rhesus monkeys and fish), thermal stability and thus the possibility of
3) high thermal stability and thus the possibility of processing in extruders, and
4) great resistance to hydrolysis.

Almost all the known processes for preparing ascorbic acid monophosphate have the disadvantage that they are suitable only for the small scale because the described working up is much too elaborate for industrial implementation. The problem is that the required product has to be separated from a large excess of inorganic salts deriving from the phosphorylation process. Thus, for example, the phosphorylation process of DE-A 27 19 303 results in a solution which contains about 4.5 equivalents of KCl and 1.8 equivalents of $K_3PO_4$, i.e. in a total of about 6 equivalents of inorganic salts, per equivalent of required product.

The process of JP-A 77890/88 was a step forward from this prior art and comprised the purification of L-ascorbate 2-phosphates by removing the impurities in an aqueous solution of L-ascorbate 2-phosphate by electrodialysis. In this process, the L-ascorbate 2-phosphate is finally precipitated and isolated as magnesium salt. The disadvantage of this process is that either a large excess of magnesium salts must be used (cf. Example 1) or else large amounts of cation exchangers must additionally be used (cf. Examples 2 and 3). In addition, the magnesium L-ascorbate 2-phosphate which is the product of this process has certain disadvantages in the isolation, for example a relatively high filtration resistance, a tendency to aggregate on drying and the formation of dust when used subsequently.

It is an object of the present invention to remove in an even more advantageous manner impurities from the solution of potassium L-ascorbate 2-phosphate which is obtained after the phosphorylation of isopropylidene-L-ascorbic acid (IPAA) with $POCl_3$ and after removal of auxiliaries and part of the inorganic salts which are formed, and which is heavily contaminated with KCl, and, in this way, to isolate the L-ascorbate 2-phosphate in the form of a more easily handled salt.

We have found that this salt is achieved, surprisingly, by a process in which it is possible to remove excess salts satisfactorily from ascorbate 2-phosphate solutions which, besides excess KCl, contain $MgCl_2$ in an amount which is only about equivalent to that of ascorbate 2-phosphate, by conventional electrodialysis without large losses of desired product. In this process there is a very great shift in the cation ratio in favor of $Mg^{2+}$, which results in a mixed potassium/magnesium salt and an almost selective reduction in the concentration of excess KCl.

We have also found, surprisingly, that potassium magnesium L-ascorbate 2-phosphate, which has not previously been described, has particularly advantageous properties. It precipitates in a well-crystallized form from solutions. This means that its filtration properties are extremely good and it has no tendency to aggregate on drying (cf. Example 1). It has a defined content of water of crystallization and is not hygroscopic. Since it contains only 3 molecules, not the 5 in the pure magnesium salt, of water of crystallization per molecule of ascorbate, the vitamin C content of the dry powder is higher.

Based on these findings, a process which allows L-ascorbate 2-phosphate solutions to be purified by electrodialysis more advantageously and the L-ascorbate 2-phosphate to be isolated in the form of a more easily handled salt.

Hence the present invention relates to a process for preparing potassium magnesium L-ascorbate 2-phosphate from an aqueous solution of potassium L-ascorbate 2-phosphate which is heavily contaminated with potassium chloride, which comprises adding to the aqueous solution of potassium L-ascorbate 2-phosphate sufficient magnesium chloride for the solution to contain about 0.9 to 1.3 equivalents, preferably from 0.95 to 1.1 equivalents, of magnesium ions per equivalent of potassium L-ascorbate 2-phosphate, substantially removing the potassium chloride present in the solution by electrodialysis, and isolating the potassium magnesium L-ascorbate 2-phosphate from the remaining solution by crystallization in a conventional manner.

The novel process is very particularly suitable for preparing potassium magnesium L-ascorbate 2-phosphate from an aqueous solution of potassium L-ascorbate 2-phosphate resulting from the phosphorylation of 5,6-isopropylidene-L-ascorbic acid with phosphorus oxychloride, subsequent precipitation of the excess phosphoric acid as $KMgPO_4$ with magnesium chloride, removal by distillation of the base employed in the phosphorylation, treatment of the reaction mixture with hydrochloric acid to eliminate the isopropylidene protective group, and removal of the potassium chloride which crystallizes on subsequent cooling.

For technical reasons it is advisable to employ the magnesium chloride in the form of an aqueous solution in the process according to the invention.

Particularly good yields are obtained from the process according to the invention when the aqueous L-ascorbate 2-phosphate solution is adjusted to a pH of from 5 to 8, preferably 6 to 7, during the electrodialysis. It is particularly advantageous to adjust the pH to the preferred value by adding KOH. It is not necessary for potassium and magnesium to be present in exactly the stoichiometric ratio in the mixed salt prepared according to the invention. The potassium/magnesium ratio in the solution from which the mixed salt is precipitated is virtually identical to that of the crystalline product obtained therefrom. The results of the isolation of ascorbic acid 2-phosphate in the form of a potassium/magnesium mixed salt are optimal when the composition of the salt is approximately $K_{1\pm0.3}Mg_{1\pm0.15}$ ascorbate 2-phosphate.

A salt of this composition is obtained from the process according to the invention when the concentration of potassium chloride in the solution of potassium L-ascorbate 2-phosphate to which magnesium chloride has been added is reduced by electrodialysis until the $Mg^{2+}/K^+$ equivalent ratio is from 3.3 to 1.3.

A salt of the stoichiometric composition KMg ascorbate 2-phosphate is obtained when sufficient magnesium chloride is added to the solution of potassium L-ascorbate 2-phosphate for the solution to contain from 0.9 to 1.3 equivalents of magnesium ions per mole of L-ascorbate 2-phosphate, and the concentration of potassium chloride in the solution is reduced by electrodialysis until the magnesium/potassium equivalent ratio in the solution is about 2:1.

The present invention also relates to a particularly advantageous overall process for preparing potassium magnesium L-ascorbate 2-phosphate as claimed in claim 1, which comprises A) 5,6-isopropylidene-L-ascorbic acid is reacted with $POCl_3$ in a suitable aqueous solvent while maintaining a pH of from 8 to 13.5 using KOH and in the presence of a tertiary amine at from $-10°$ to $+25°$ C., B) from 90 to 110 mol %, based on the inorganic phosphate present in the reaction mixture, of magnesium chloride is added to the reaction mixture from the phosphorylation without previous treatment with ion exchanger, C) the crystallized $KMgPO_4$ is separated off, D) the resulting filtrate is adjusted to a pH of about 7 with HCl and subsequently distilled to remove the tertiary amine with part of the water, E) the resulting concentrate is acidified to a pH of about 1 with HCl and stirred at from 30° to 40° C. for about 2 hours and, where appropriate F) sufficient magnesium chloride is added to the solution resulting after cooling and removal of the crystallized potassium chloride for the solution to contain from 0.9 to 1.3 equivalents of magnesium ions per equivalent of ascorbate 2-phosphate, and the solution is adjusted to a pH of from 6 to 7 with KOH, G) the concentration of potassium chloride in the solution is reduced by electrodialysis until the magnesium to potassium equivalent ratio at a pH of from 6 to 7 is from 3.3 to 1.3:1, preferably about 2:1, and H) the resulting potassium magnesium L-ascorbate 2-phosphate is isolated from the resulting aqueous solution by concentration and/or treatment with methanol, ethanol or acetone.

The process according to the invention has great advantages for the preparation of salts of L-ascorbic acid 2-phosphate.

1) The resulting salt has distinctly better handling properties (cf. Example 1) and a higher vitamin C content.

2) The salt load in the reaction mixture to be removed during working up is considerably reduced because, surprisingly, it is necessary to add only equivalent amounts of magnesium chloride. This greatly reduces the current consumption in the electrodialysis.

3) There is no need to use ion exchangers as was necessary in the process of JP-A 77890/88 (cf. Examples 2 and 3).

4) The losses of the required product are extremely low when the preferred conditions are employed (solution at pH 6–7 during the electrodialysis).

5) The salt obtained after the treatment with HCl and the electrodialysis is only slightly impure potassium chloride which can be used without further treatment for fertilizer production.

The following additional information on the procedure for the advantageous overall process is given hereinafter.

The loss of required product during the reduction in the KCl concentration by electrodialysis of a potassium L-ascorbate 2-phosphate solution which is heavily contaminated with KCl is minimal only when the amount of magnesium ions present is approximately equivalent to the ascorbate 2-phosphate content. There are distinct losses of required product when the amounts are smaller. Substantially larger amounts result in salts which crystallize poorly, in an increase in the current consumption because they have to be removed again by electrodialysis, and in larger losses of required product because the running times are longer. It is possible, by modifying the process to use particularly advantageous electrodialysis conditions, to result in only about ⅓ equivalent of $K^+$ and ⅔ equivalent of $Mg^2$ per equivalent of ascorbate 2-phosphate in the solution after electrodialysis. While the $Cl^-$ content has been reduced to less than 0.02 equivalent/kg ($\approx 0.07\%$ weight). The current consumption is particularly low in the process according to the invention. The product losses are no more than 1 to 2%. The losses of required product are greatly influenced not only by the $Mg^{2+}$ content but also by the pH of the mixture during electrodialysis. A pH of about 6 to 7 has proven particularly advantageous in this respect.

The phosphorylation of 5,6-isopropylidene-L-ascorbic acid is advantageously carried out by the process of Seib (cf. DE-A 27 19 303), i.e. by reaction with $POCl_3$ in the presence of a tertiary amine in a suitable aqueous solvent at from $-10°$ to $25°$ C. while maintaining a pH of about 8 to 13.5, preferably 10 to 13, by adding KOH throughout the phosphorylation reaction.

Suitable tertiary amines are those which are miscible with the reaction mixture and non-volatile and have an ionization constant of less than about $10^7$. Examples are lower trialkylamines such as triethylamine, and cyclic amines such as pyridine.

The best yields are obtained with pyridine. The molar quantity of amine is about 5 times that of the ascorbic acid.

The phosphorylation is particularly advantageously carried out with an amine concentration in the reaction mixture of about 1.5 to 3 moles, preferably 2.2 to 2.6 moles, and an ascorbic acid concentration of about 0.3 to 0.6 mole, preferably 0.4 to 0.5 mole, per liter.

Water is advantageously used as solvent.

The reaction temperature should generally be the lowest at which the reaction mixture is still liquid and the tertiary amine does not form a separate phase. Suitable temperatures are from $-10°$ to $+10°$ C.

Then, in order to remove the excess inorganic phosphate, an amount of $MgCl_2$, preferably an aqueous solution of $MgCl_2$, which is approximately equivalent to the amount of excess inorganic phosphate is added to the mixture resulting from the phosphorylation reaction, directly and without previous treatment with ion exchanger, at a pH>7.

The KMgPO$_4$ which crystallizes is separated off.

The resulting filtrate is then neutralized with HCl and distilled under reduced pressure to remove the base used in the phosphorylation together with part of the water.

The isopropylidene group is advantageously eliminated at this stage in the process by acidifying the concentrated solution to pH 1 with concentrated HCl and maintaining the mixture at from about 10° to 60° C., preferably 30° to 40° C., while stirring and distilling out acetone, for from 1 to 20, preferably about 1.5 to 2.5 hours. Besides the elimination of acetone, this HCl treatment has the advantage that the ascorbate diphosphates, triphosphates and polyphosphates formed in the reaction with POCl$_3$ are hydrolyzed to ascorbate monophosphate and then about ⅓ of the KCl present in the solution crystallizes on cooling. This can be used for fertilizers without further purification.

The filtrate obtained by removing crystallized KCl is very suitable for the preparation according to the invention of potassium magnesium L-ascorbate 2-phosphate by electrodialysis.

To minimize the loss of required product, the solution is first mixed with the required amount of MgCl$_2$ and then adjusted to a pH of from 5 to 8, preferably 6 to 7. It is advantageous, although not obligatory, to carry out this pH adjustment with aqueous KOH.

Before the electrodialysis the content of Mg$^{2+}$ ions should be from 0.9 to 1.3 equivalents, preferably 0.95 to 1.1 equivalents, per equivalent of ascorbate monophosphate.

The removal of salts from aqueous salt solutions by electrodialysis and appropriate equipment for this are known and are described, for example, in H. Strathmann "Trennung von molekularen Mischungen mit Hilfe synthetischer Membranen", Steinkopf Verlag, Darmstadt, 1979, pages 76 to 86, and in D. S. Flett "Ion Exchange Membranes", Ellis Horwood, Chichester 1983, pages 179 to 191.

In the present invention the electrodialysis is expediently carried out in such a way that anion and cation exchanger membranes are arranged alternately in parallel between two electrodes and the chambers formed by spacer frames placed between them are sealed against each other, and the KCl- and MgCl$_2$-containing, pH-adjusted product solution (also called diluate hereinafter) is passed through those chambers having an anion exchanger membrane on the anode side, and an aqueous KCl solution (also called concentrate hereinafter) is passed through those chambers which have a cation exchanger membrane on the anode side.

The cathode and anode spaces are separated from the diluate and concentrate chambers by the last membrane in each case, preferably a cation exchanger membrane. An electrolyte solution is advantageously passed over the electrodes during the electrodialysis in order to remove from the electrode chambers the gases which are produced. The electrode washing solution is expediently an aqueous 1–10% by weight sodium sulfate solution.

The ion exchanger membranes which can be employed are commercial standard membranes which, for example, are from 0.1 to 1 mm thick and have a pore diameter of from 1 to 30 μm or a gel-like structure, a permselectivity >0.9 and an electrical resistance of about 5 Ωcm$^2$ (Desalination 34 (1980) 77–95).

The anion exchanger membranes are normally composed of a matrix polymer which contains chemically bonded cationic groups, while the cation exchanger membranes comprise a matrix polymer with anionic groups. Examples of ion exchange membranes of the said types are the strongly basic and strongly acidic polystyrene-based membranes obtainable under the names SELEMION® (Asahi Glass), NEOSEPTA® (Tokoyama Soda) or IONAC® (Ionac Chemical Company).

The electrodialysis in the process according to the invention is generally carried out at up to 100° C., preferably from 15° to 80° C., with a current density which usually does not exceed 3000 A/m$^2$, preferably from 10 to 1000 A/m$^2$, until the desired decrease in Cl concentration and the desired Mg$^{2+}$/K$^+$ ratio have been achieved. The DC voltage required for ion transport through the membranes depends on the conductivities of the diluate and concentrate and the distance between the membranes, which is determined by the spacer frames used in the construction of the electrodialysis cell.

The process can be carried out either continuously with several stacks of membranes arranged in series or batchwise by circulating the liquids using buffer vessels, or by combinations of these.

The required potassium magnesium L-ascorbate 2-phosphate can be isolated as crystals from the solution after electrodialysis by concentration and/or treatment with solvents such as methanol, ethanol or acetone.

The process according to the invention can be used to prepare and isolate potassium magnesium L-ascorbate 2-phosphate in a very advantageous manner. Potassium magnesium L-ascorbate 2-phosphate is a novel salt of L-ascorbic acid 2-phosphate and can be isolated and handled very easily.

EXAMPLE 1

To demonstrate the advantageous properties of the novel potassium magnesium L-ascorbate 2-phosphate by comparison with potassium L-ascorbate 2-phosphate and magnesium L-ascorbate 2-phosphate, the filtration resistance, the aggregation on drying and the formation of dust by potassium magnesium L-ascorbate 2-phosphates of the formula K$_x$Mg$_y$C$_6$H$_6$PO$_9$×3 H$_2$O, i.e. salts with different K/Mg ratios, were compared with the corresponding properties of the potassium salt (x=3; y=0) and of the magnesium salt (x=0; y=1.5). The results are shown in the following table.

| Experiment | x | y | Filtration resistance | Aggregation on drying | Dust formation |
|---|---|---|---|---|---|
| a) | 0.00 | 1.50 | +++ | +++ | +++ |
| b) | 0.08 | 1.46 | +++ | +++ | +++ |
| c) | 0.17 | 1.42 | +++ | ++ | ++ |
| d) | 0.27 | 1.37 | ++ | ++ | ++ |
| e) | 0.36 | 1.32 | ++ | + | ++ |
| f) | 0.48 | 1.26 | + | + | + |
| g) | 0.61 | 1.20 | − | − | + |
| h) | 0.75 | 1.12 | − | − | + |
| i) | 0.83 | 1.09 | − | − | + |
| j) | 1.08 | 0.96 | − | − | + |
| k) | 1.20 | 0.86 | − | − | + |
| l) | 1.54 | 0.73 | + | + | − |
| m) | 1.86 | 0.57 | + | + | − |
| n) | 2.15 | 0.43 | + | ++ | − |
| o) | 3.00 | 0.00 | Product is oil | | | the experiments showed that salts of the composition $K_{1\pm0.3}Mg_{1\pm0.15}$ ascorbate 2-phosphate have the best properties.

Evaluation scale:

| | |
|---|---|
| +++ | very high |
| ++ | high |
| + | average |
| − | low |

EXAMPLE 2

Desalting Procedure and Results

The apparatus comprised an electrodialysis (ED) cell and three circulations (for diluate, concentrate and electrode washing solution). Each of these circulations was equipped with a magnetic centrifugal pump, a heat exchanger and a reservoir (1 to 10 l) and connected via tubing to the ED cell.

1 kg of synthesis solution with the composition evident from Table 1, and a test solution which contained equivalent amounts of KCl and $MgCl_2$.

Concentrate: 1 kg of an approximately 0.25% strength aqueous KCl solution.

Electrode washing solution: 2 kg of a 5% by weight $Na_2SO_4$ solution.

The solutions were circulated through the ED cell by the pump and electrodialyzed at about 40° C. with a cell voltage up to 30 V and a current up to 3 A. The flow rates for the diluate and concentrate were about 1 kg/min.

The changes in current and voltage were evident from the resistance in the ED system. A current of 3 A was possible below a cell voltage of 30 V, while the current decreased accordingly if 30 V was reached during the ED owing to an increase in the resistance.

The process was stopped when the required degree of desalting was reached. The results are compiled in Table 1.

TABLE 1 electrodialysis results

| Example | 2a (Comparative) | | 2b (Comparative) | | 2c | | 2d | | 2e | | 2f (Comparative) | |
|---|---|---|---|---|---|---|---|---|---|---|---|---|
| Electrodialysis time (h) | E* | A** | E* | A** | E* | A** | E* | A** | E* | A** | E* | A** |
| | 2.25 | | 3.0 | | 2.25 | | 2.67 | | 2.5 | | 3.5 | |
| Diluate | | | | | | | | | | | | |
| Amount (g) | 1005 | 605 | 999 | 512 | 1054 | 692 | 1081 | 662 | 1014 | 629 | 1000 | 789 |
| Conductivity (mS/cm) | 121 | 8.2 | 221 | 14 | 185 | 22 | 190 | 14 | 180 | 25 | 157 | 0.6 |
| pH | 6.5 | 7.0 | 4.4 | 5.0 | 6.0 | 6.5 | 6.3 | 6.8 | 3.2 | 3.6 | 7.4 | 4.1 |
| $K^+$ (eq/kg) | 1.43 | 0.08 | 2.56 | 0.09 | 2.46 | 0.43 | 2.43 | 0.22 | 2.17 | 0.21 | 1 | <0.01 |
| $Mg^{2+}$ (eq/kg) | 0.63 | 0.80 | 0.53 | 0.77 | 0.82 | 1.15 | 1.07 | 1.48 | 0.90 | 0.90 | 1 | <0.01 |
| $Cl^-$ (eq/kg) | 1.35 | 0.01 | 2.48 | 0.01 | 2.09 | 0.02 | 2.43 | 0.01 | 2.20 | 0.03 | 2 | 0.01 |
| AAMP (eq/kg) | 0.77 | 0.98 | 0.68 | 0.98 | 0.84 | 1.27 | 0.86 | 1.37 | 0.87 | 1.29 | 0 | 0 |
| eq $Mg^{2+}$/eq $AAMP^{3-}$ | 0.82 | 0.81 | 0.78 | 0.79 | 0.98 | 0.91 | 1.24 | 1.08 | 1.03 | 0.70 | — | — |
| eq $Mg^{2+}$/eq $K^+$ | 0.44 | 10.0 | 0.21 | 8.6 | 0.33 | 2.7 | 0.44 | 6.7 | 0.41 | 4.29 | 1 ca. | 1 |
| Concentration decrease in the diluate | | | | | | | | | | | | |
| $K^+$ (%) | 96.6 | | 98.2 | | 88.5 | | 94.5 | | 94.0 | | >99.2 | |
| $Mg^{2+}$ (%) | 23.6 | | 25.5 | | 7.9 | | 15.3 | | 38.0 | | >99.2 | |
| $Cl^-$ (%) | 99.6 | | 99.8 | | 99.4 | | 99.7 | | 99.2 | | 99.6 | |
| $AAMP^{3-}$ (%) | 23.4 | | 26.1 | | 0.7 | | 2.4 | | 8.0 | | — | |

*initial
**final

The ED cell had two platinum electrodes each with an area of 35 cm². The electrode spaces were separated from the adjoining concentrate chambers by Nafion ® cation exchanger membranes (from Du Pont). Between the electrode chambers there were 11 concentrate and 10 diluate chambers arranged alternately. The chambers were separated from one another alternately by Selemion ®AMV and Selemion CMV membranes (from Asahi Glass). All the membranes had an active area of 37 cm². The membranes were 0.5 mm apart. Inflow and outflow of the particular solutions were possible through appropriate connecting orifices in the sealing frames and in the endplates and connections with the appropriate circuits.

The apparatus was equipped with a DC supply and instruments for measuring the temperature, pH, voltage, current and conductivity and with a pH-controlled acid metering system. The desalting was carried out batchwise.

The following solutions were used in the electrodialysis apparatus circulations:
Diluate:

The optimal result of the process according to the invention was achieved in Example 2c. The synthesis solution used had an $Mg^{2+}/AAMP^{3-}$ equivalent ratio of about 1 and a pH of 6. The solution obtained after the reduction in the Cl concentration was almost complete (99.4%) is concentrated by a factor of 1.5, has an $Mg^{2+}/K^+$ ratio of 2.7 and contains 0.18 eq/kg $PO_4^{3-}$ (from the non-quantitative $KMgPO_4$ precipitation). Concentration of this solution and precipitation with methanol yielded a mixed potassium/magnesium salt with the composition $K_{1\pm0.3}Mg_{1\pm0.15}AAMP$. The loss of $AAMP^{3-}$ during the desalting was only about 1%.

Comparative Examples 2a and 2b show the effect of a lower initial $Mg^{2+}/AAMP^{3-}$ equivalent ratio (0.8), and Example 2d shows that of one higher (1.24) than in Example 2c.

Drastic losses of the required product were found in Comparative Examples 2a and 2b.

Example 2e shows that use of a synthetic solution with an $Mg^{2+}/AAMP^{3-}$ equivalent ratio of about 1 and a pH lowered to 3.2 results in a distinct increase in the loss of $AAMP^{3-}$ (from 0.7 to 8%).

Comparative Example 2f is intended to illustrate the surprising effect, namely the almost selective removal of KCl from a $K^+/Mg^{2+}/Cl^-/AAMP^{3-}$ mixture (as specified in Example 2c), by comparison with a solution which contains only KCl and $MgCl_2$ and no $AAMP^{3-}$. It is evident that desalting of a mixed $KCl/MgCl_2$ solution results in removal of both salts in the same way.

EXAMPLE 3 a) Preparation of 5,6-isopropylideneascorbic acid (IPAA)

43.1 g of 24% oleum were added dropwise to 480 ml (6.55 mol) of acetone at from $-10°$ to $0°$ C. Then 120.6 g (0.68 mol) of powdered ascorbic acid were added, and the resulting suspension was stirred at $0°$ C. for 5.5 hours (h). The mixture was then cooled to $-10°$ C. and filtered through a sintered disk, the mother liquor was sucked off, and the filter cake was dried by water pump suction for 2 h. The yield was 146 g (98.6% of theory).

b) Phosphorylation with $POCl_3$

The 146 g of IPAA (680 mmol) obtained as in a) were introduced into an $O_2$-free solution of 300 ml of pyridine in 1200 ml of water while the pH of the solution was maintained at 8 (Dulcometer) by metering in 50% strength aqueous KOH. The pH of the solution was then adjusted to 13 with KOH and maintained at this while, at $0°-10°$ C., 146.4 g (955 mmol) of $POCl_3$ were slowly metered in, and the resulting mixture was then stirred for 15 minutes (min).

c) Precipitation of $KMgPO_4$

The reaction mixture obtained in b) was mixed with 69 g of $MgCl_2.6H_2O$ (340 mmol) in the form of a 15% strength aqueous solution and then cooled to room temperature (RT) and the crystals of $KMgPO_4$ were filtered off with suction and washed with $2\times 200$ ml of water. After drying ($50°$ C., 100 mbar) the crystals had the composition $KMgPO_4\times 5H_2O$.

Yield 85 g (342 mmol).

d) Removal of pyridine from the reaction mixture

The filtrate obtained in c) was adjusted to pH 7 with 37% strength aqueous HCl and concentrated to 1000 g in a Sambay evaporator under reduced pressure. The resulting condensate contained more than 99% of the pyridine in aqueous solution.

e) Elimination of the isopropylidene protective group and precipitation of KCl

The concentrate (1000 g) obtained in d), which already contained some solid KCl, was adjusted to pH 1 with 116 g of 37% strength HCl in the warm and was stirred at from $30°$ to $40°$ C. for 2 h. The mixture was then cooled to $0°$ C., stirred for 30 min, filtered to remove the crystals, and the latter were washed with $2\times 100$ ml of ice-water. This resulted in 171 g (1156 mmol) of pure KCl.

f) Electrodialysis

The filtrate resulting from e) was mixed with 206 g of $MgCl_2.6H_2O$ (1020 mmol) in the form of a 15% strength aqueous solution, and the pH was adjusted to 6 to 7 with KOH.

Reaction mixture: 1667 g

Vitamin C content: 109.6 g of C in total ($\equiv 90.9\%$ based on ascorbic acid)

93.7 g of C as ascorbate 2-phosphate (77.7%)

15.9 g of C as bisascorbate 2-phosphate (13.2%).

This solution was desalted by batchwise electrodialysis under the conditions specified in Example 2.

This resulted in 1095 g of mixture containing 108.1 g of C in total ($\equiv 89.6\%$ based on ascorbic acid)

93.0 g of C as ascorbate 2-phosphate (77.1%) and 15.1 g of C as bisascorbate 2-phosphate (12.5%).

The desalted mixture was concentrated to 390 g (rotary evaporator) and immediately added dropwise to 800 ml of stirred methanol in the warm. The crystals which formed after cooling to RT were filtered off with suction, and the filter cake was washed with $2\times 150$ ml of methanol and dried under a stream of $N_2$.

The result was 230.0 g of $K_{0.8}Mg\ C_6H_6PO_9\times 3.5\text{-}H_2O$; vitamin C content=46.9% (HPLC) containing 107.5 g of C in total ($\equiv 89.1\%$ based on ascorbic acid)

92.9 g of C as ascorbate 2-phosphate (77.1%)

13.9 g of C as bisascorbate 2-phosphate (11.5%).

The total yield over all these stages was 89.1% of theory based on ascorbic acid.

We claim:

1. A process for preparing potassium magnesium L-ascorbate 2-phosphate from an aqueous solution of potassium L-ascorbate 2-phosphate which is heavily contaminated with potassium chloride, which comprises adding to the aqueous solution of potassium L-ascorbate 2-phosphate sufficient magnesium chloride for the solution to contain about 0.90 to 1.3 equivalents of magnesium ions per equivalent of L-ascorbate 2-phosphate, substantially removing the potassium chloride present in the solution by electrodialysis, and isolating the potassium magnesium L-ascorbate 2-phosphate from the remaining solution by crystallization.

2. A process for preparing potassium magnesium L-ascorbate 2-phosphate as defined in claim 1, wherein the solution of potassium L-ascorbate 2-phosphate which is heavily contaminated with potassium chloride is one resulting from the phosphorylation of 5,6-isopropylidene-L-ascorbic acid with phosphorus oxychloride, subsequent precipitation of the excess phosphoric acid as $KMgPO_4$ with magnesium chloride, removal by distillation of the base employed in the phosphorylation, treatment of the reaction mixture with hydrochloric acid to eliminate the isopropylidene protective group, and removal of the potassium chloride which crystallizes on cooling the solution.

3. A process for preparing potassium magnesium L-ascorbate 2-phosphate as defined in claim 1, wherein sufficient magnesium chloride is added to the aqueous solution of potassium L-ascorbate 2-phosphate for the solution to contain from 0.95 to 1.10 equivalents of magnesium ions per equivalent of L-ascorbate 2-phosphate.

4. A process for preparing potassium magnesium L-ascorbate 2-phosphate as defined in claim 1, wherein the aqueous solution of potassium L-ascorbate 2-phosphate has a pH of from 5 to 8.

5. A process for preparing potassium magnesium L-ascorbate 2-phosphate as defined in claim 1, wherein the aqueous solution of potassium L-ascorbate 2-phosphate has been adjusted to a pH of from 6 to 7 with KOH.

6. A process for preparing potassium magnesium L-ascorbate 2-phosphate as defined in claim 1, wherein the concentration of potassium chloride in the solution of potassium L-ascorbate 2-phosphate which has been mixed with magnesium chloride is reduced by electrodialysis until the $Mg^{2+}/K^+$ equivalent ratio is from 3.3 to 1.3.

7. A process for preparing potassium magnesium L-ascorbate 2-phosphate as defined in claim 3, wherein the concentration of potassium chloride in the solution of potassium L-ascorbate 2-phosphate which has been mixed with magnesium chloride is reduced by electrodialysis until the $Mg^{2+}/K^+$ equivalent ratio is about 2.

8. A process for preparing potassium magnesium L-ascorbate 2-phosphate as defined in claim 1, wherein the potassium magnesium L-ascorbate 2-phosphate is isolated from the solution remaining after electrodialysis by concentration and/or treatment with methanol, ethanol or acetone.

9. A process for preparing potassium magnesium L-ascorbate 2-phosphate as defined in claim 1, wherein the magnesium chloride is used in the form of an aqueous solution.

10. A process for preparing potassium magnesium L-ascorbate 2-phosphate as defined in claim 1, wherein
   A) 5,6-isopropylidene-L-ascorbic acid is reacted with $POCl_3$ in a suitable aqueous solvent while maintaining a pH of from 8 to 13.5 using KOH and in the presence of a tertiary amine at from $-10°$ to $+25°$ C.,
   B) from 90 to 110 mol %, based on the inorganic phosphate present in the reaction mixture, of magnesium chloride is added to the reaction mixture from the phosphorylation without previous treatment with ion exchanger,
   C) the crystallized $KMgPO_4$ is separated off,
   D) the resulting filtrate is adjusted to a pH of about 7 with HCl and subsequently distilled to remove the tertiary amine and part of the water,
   E) the resulting concentrate is acidified to a pH of about 1 with HCl and stirred at from 30° to 40° C. for about 2 hours,
   F) sufficient magnesium chloride is added to the solution resulting after cooling and removal of the crystallized potassium chloride for the solution to contain from 0.9 to 1.3 equivalents of magnesium ions per equivalent of ascorbate 2-phosphate, and the solution is adjusted to a pH of from 6 to 7 with KOH,
   G) the concentration of potassium chloride in the solution is reduced by electrodialysis until the $Mg^{2+}/K^+$ equivalent ratio at a pH of from 6 to 7 is from 3.3 to 1.3:1 and
   H) the resulting potassium magnesium L-ascorbate 2-phosphate is isolated from the resulting aqueous solution by concentration and/or treatment with methanol, ethanol or acetone.

* * * * *